United States Patent
Brown et al.

(10) Patent No.: US 9,180,145 B2
(45) Date of Patent: Nov. 10, 2015

(54) COMPOSITIONS AND METHODS FOR RECRUITING AND LOCALIZING STEM CELLS

(71) Applicant: MiMedx Group, Inc., Marietta, GA (US)

(72) Inventors: Rebeccah J. C. Brown, Marietta, GA (US); Thomas J. Koob, Marietta, GA (US); Guilhem Denozière, Marietta, GA (US)

(73) Assignee: MiMedx Group, Inc., Marietta, GA (US)

( * ) Notice: Subject to any disclaimer, the term of this patent is extended or adjusted under 35 U.S.C. 154(b) by 0 days.

(21) Appl. No.: 14/050,218

(22) Filed: Oct. 9, 2013

(65) Prior Publication Data

US 2014/0140964 A1 May 22, 2014

Related U.S. Application Data

(63) Continuation-in-part of application No. 13/815,873, filed on Mar. 15, 2013.

(60) Provisional application No. 61/713,352, filed on Oct. 12, 2012.

(51) Int. Cl.
*C12N 5/071* (2010.01)
*A61K 35/50* (2015.01)
*C12N 5/00* (2006.01)

(52) U.S. Cl.
CPC .. *A61K 35/50* (2013.01); *C12N 5/00* (2013.01)

(58) Field of Classification Search
None
See application file for complete search history.

(56) References Cited

U.S. PATENT DOCUMENTS

| | | | |
|---|---|---|---|
| 2,694,914 A | 11/1954 | Glover, Jr. | |
| 3,272,204 A | 9/1966 | Artandi | |
| 4,564,368 A | 1/1986 | Sawyer et al. | |
| 4,703,108 A | 10/1987 | Silver et al. | |
| 4,745,771 A | 5/1988 | Linner et al. | |
| 4,968,325 A | 11/1990 | Black et al. | |
| 5,118,867 A | 6/1992 | Bahrmann et al. | |
| 5,284,655 A | 2/1994 | Bogdansky et al. | |
| 6,030,635 A | 2/2000 | Gertzman et al. | |
| 6,387,369 B1 | 5/2002 | Pittenger et al. | |
| 6,565,960 B2 | 5/2003 | Koob et al. | |
| 6,936,271 B1 | 8/2005 | Oliver et al. | |
| 7,311,904 B2 | 12/2007 | Hariri | |
| 7,311,905 B2 | 12/2007 | Hariri | |
| 7,901,455 B2 | 3/2011 | Koob et al. | |
| 8,067,044 B2 | 11/2011 | Henry et al. | |
| 8,153,162 B2 | 4/2012 | Tseng et al. | |
| 8,177,839 B2 | 5/2012 | Koob et al. | |
| 8,192,481 B2 | 6/2012 | King | |
| 8,323,701 B2 | 12/2012 | Daniel et al. | |
| 8,357,403 B2 | 1/2013 | Daniel et al. | |
| 8,372,437 B2 | 2/2013 | Daniel | |
| 8,372,439 B2 | 2/2013 | Daniel et al. | |
| 8,409,626 B2 | 4/2013 | Daniel et al. | |
| 2002/0123141 A1 | 9/2002 | Hariri | |
| 2002/0160510 A1 | 10/2002 | Hariri | |
| 2003/0032179 A1 | 2/2003 | Hariri | |
| 2003/0187515 A1 | 10/2003 | Hariri et al. | |
| 2004/0028711 A1 | 2/2004 | Uchida et al. | |
| 2004/0048796 A1 | 3/2004 | Hariri et al. | |
| 2006/0140913 A1 | 6/2006 | Bhatia | |
| 2006/0166361 A1 | 7/2006 | Seyda et al. | |
| 2006/0210532 A1 | 9/2006 | Carmeliet et al. | |
| 2007/0020225 A1 | 1/2007 | Abramson et al. | |
| 2007/0021762 A1 | 1/2007 | Liu et al. | |
| 2007/0071740 A1 | 3/2007 | Tseng et al. | |
| 2007/0071828 A1 | 3/2007 | Tseng et al. | |
| 2007/0202189 A1 | 8/2007 | Ahlfors | |
| 2007/0248575 A1 | 10/2007 | Connor et al. | |
| 2007/0299043 A1 | 12/2007 | Hunter et al. | |
| 2008/0046095 A1 | 2/2008 | Daniel | |
| 2008/0050347 A1 | 2/2008 | Ichim | |
| 2008/0069895 A1 | 3/2008 | Liu et al. | |
| 2008/0131966 A1 | 6/2008 | Hariri | |
| 2008/0181967 A1 | 7/2008 | Liu et al. | |
| 2008/0233552 A1 | 9/2008 | Ma et al. | |
| 2009/0012629 A1 | 1/2009 | Yao et al. | |
| 2009/0036996 A1 | 2/2009 | Roeber | |
| 2009/0053290 A1 | 2/2009 | Sand et al. | |
| 2009/0142831 A1 | 6/2009 | Hariri | |
| 2009/0287308 A1 | 11/2009 | Davis et al. | |

(Continued)

FOREIGN PATENT DOCUMENTS

CN  101433556  5/2009
EP  0 431 164  6/1991

(Continued)

OTHER PUBLICATIONS

U.S. Appl. No. 13/647,308, filed Oct. 8, 2012, Daniel et al.
U.S. Appl. No. 13/719,148, filed Feb. 13, 2012, Morse et al.
U.S. Appl. No. 13/744,331, filed Jan. 17, 2013, Koob et al.
U.S. Appl. No. 13/745,642, filed Jan. 18, 2013, Koob et al.
U.S. Appl. No. 13/787,612, filed Mar. 6, 2013, Morse et al.
U.S. Appl. No. 13/815,747, filed Mar. 15, 2013, Daniel et al.
U.S. Appl. No. 13/815,784, filed Mar. 15, 2013, Koob et al.

(Continued)

*Primary Examiner* — Robert Mondesi
*Assistant Examiner* — Thomas J Visone
(74) *Attorney, Agent, or Firm* — Foley & Lardner, LLP

(57) ABSTRACT

Described herein are compositions and methods of using modified placental tissue to achieve endogenous and exogenous therapeutic effects. When applied to an injured or diseased organ or body part, the modified placental tissue elicit stem cell recruitment and/or localization directly to or proximate to the site of application. Also described is a novel vacuum drying device and the use thereof.

7 Claims, 7 Drawing Sheets

(56) References Cited

U.S. PATENT DOCUMENTS

| | | |
|---|---|---|
| 2009/0291891 A1 | 11/2009 | Neufeld |
| 2010/0028849 A1 | 2/2010 | Shelby et al. |
| 2010/0104539 A1 | 4/2010 | Daniel et al. |
| 2010/0136114 A1 | 6/2010 | Mao |
| 2010/0143312 A1 | 6/2010 | Hariri et al. |
| 2010/0178297 A1 | 7/2010 | Carmeliet et al. |
| 2010/0209408 A1 | 8/2010 | Stephen et al. |
| 2010/0260847 A1 | 10/2010 | Hariri |
| 2010/0272782 A1 | 10/2010 | Owens et al. |
| 2011/0044997 A1 | 2/2011 | Rankin et al. |
| 2011/0177150 A1 | 7/2011 | Pathak et al. |
| 2011/0189301 A1 | 8/2011 | Yang et al. |
| 2011/0206776 A1 | 8/2011 | Tom et al. |
| 2011/0282448 A1 | 11/2011 | Paulos et al. |
| 2011/0307059 A1 | 12/2011 | Young et al. |
| 2012/0010708 A1 | 1/2012 | Young et al. |
| 2012/0030963 A1 | 2/2012 | Durance et al. |
| 2012/0078378 A1 | 3/2012 | Daniel et al. |
| 2012/0189583 A1 | 7/2012 | Liu et al. |
| 2012/0189586 A1 | 7/2012 | Harrell |
| 2012/0294910 A1 | 11/2012 | Daniel et al. |
| 2013/0095060 A1 | 4/2013 | Hsieh et al. |
| 2013/0230561 A1 | 9/2013 | Daniel et al. |
| 2014/0106447 A1 | 4/2014 | Brown et al. |
| 2014/0142025 A1 | 5/2014 | Koob |
| 2014/0356451 A1 | 12/2014 | Koob |

FOREIGN PATENT DOCUMENTS

| | | |
|---|---|---|
| EP | 0431479 A1 | 6/1991 |
| EP | 0 506 207 B1 | 9/1992 |
| KR | 10/1991/0011272 | 8/1991 |
| KR | 10/1991/0011727 | 8/1991 |
| KR | 2001/100588 | 11/2001 |
| WO | WO-88/03805 A1 | 6/1988 |
| WO | WO-01/08716 A1 | 2/2001 |
| WO | WO-2004/026244 | 4/2004 |
| WO | WO-2005/017165 | 2/2005 |
| WO | WO-2007/010305 | 1/2007 |
| WO | WO-2007/076522 | 7/2007 |
| WO | WO-2009/033160 | 3/2009 |
| WO | WO-2009/048908 | 4/2009 |
| WO | WO-2009/132186 A1 | 10/2009 |
| WO | WO-2010/029344 | 3/2010 |
| WO | WO-2011/103470 | 8/2011 |
| WO | WO-2011/127117 | 10/2011 |
| WO | WO-2012/003377 | 1/2012 |
| WO | WO-2012/112410 | 8/2012 |
| WO | WO-2012/112417 A2 | 8/2012 |
| WO | WO-2012/112441 A1 | 8/2012 |

OTHER PUBLICATIONS

U.S. Appl. No. 13/815,873, filed Mar. 15, 2013, Brown et al.
U.S. Appl. No. 13/963,984, filed Aug. 9, 2013, Daniel et al.
U.S. Appl. No. 13/967,326, filed Aug. 14, 2013, Koob et al.
U.S. Appl. No. 13/983,301, filed Feb. 13, 2012, Morse et al.
"MiMedx Group Announces Launch of EpiFixTM and Hiring of Vice President, Wound Care," Mimedx Press Release (2011).
Autiero et al., "Placental growth factor and its receptor, vascular endothelial growth factor receptor-1:novel targets for stimulation of ischemic tissue revascularization and inhibition of angiogenic and inflammatory disorders," J. Thromb. Haemo., (2003), 1:1356-1370.
EpiFix Produce Brochure (2011).
Hannallah et al., "Cerebrospinal fluid leaks following cervical spine surgery," J. Bone Joint Surg. Am., (2008), 90(5):1101-1105.
Hattori et al., "Placental growth factor reconstitutes hematopoiesis by recruiting VEGFR1+ stem cells from bone-marrow microenvironment," Nat. Med., (2002), 8(8):841-849.
International Preliminary Report on Patentability for copending PCT Application No. PCT/US2012/024798, dated Feb. 1, 2013.
International Search Report and Written Opinion for copending PCT Application No. PCT/US2013/054322, dated Oct. 22, 2013.
International Search Report for copending PCT Application No. PCT/US2012/024798, dated Jun. 20, 2012.
Khan et al., "Postoperative management protocol for incidental dural tears during degenerative lumbar spine surgery: A review of 3,183 consecutive degenerative lumbar cases," Spine (Phila Pa 1976), (2006), 31(22):2609-2613.
Mayfield et al., "Watertight closure of spinal dura mater: Technical note," J. Neurosurg., (1975), 43(5):639-640.
Koob et al., "Biological properties of dehydrated human amnion-chorion composite graft: implications for chronic wound healing", International Wound Healing, 2013, 10(5):493-500.
PCT International Search Report and Written Opinion dated Jan. 9, 2014 in related PCT Patent Application No. PCT/US2013/064146.
U.S. Appl. No. 13/688,091, filed Nov. 28, 2012, Spencer et al.
U.S. Appl. No. 13/744,332, filed Jan. 17, 2013, Pringle et al.
U.S. Appl. No. 13/815,753, filed Mar. 15, 2013, Koob et al.
PCT International Search Report and Written Opinion for copending PCT Application No. PCT/US2013/054319, dated Nov. 13, 2013.
PCT International Search Report and Written Opinion for copending PCT Application No. PCT/US2013/055003, dated Nov. 19, 2013.
PCT International Search Report and Written Opinion for copending PCT Application No. PCT/US2013/054320, dated Nov. 6, 2013.
PCT International Search Report and Written Opinion for copending PCT Application No. PCT/US2012/66862, dated Feb. 12, 2013.
PCT International Search Report and Written Opinion for copending PCT Application No. PCT/US2013/054325, dated Oct. 28, 2013.
Tao, et al., "Implantation of amniotic membrane to reduce postlaminectomy epidurla adhesions," Eur. Spine. J., (2009), 18:1202-1212.
MiMedx Press Release, "MiMedx Scientific Study is Electronically Published in the International Wound Journal", 2013.
PCT International Preliminary Report on Patentability dated Jan. 16, 2014 in PCT Patent Application No. PCT/US12/66862.
Derwent Abstract for KR 200110588, original document published Nov. 2001.
http://proxybiomedical.com/Images/ML005-01-Rev002.pdf (accessed on Jun. 5, 2014).
International Search Report and Written Opinion for PCT/US2014/012141, dated May 20, 2014.
Nagaya et al., "Transplantation of mesenchymal stem cells improves cardiac function in a rat model of dilated cardiomyopathy", Circulation, 2005, 112(8):1128-1135.
Parolini et al., "Toward cell therapy using placenta-derived cells: disease mechanisms, cell biology, preclinical studies, and regulatory aspects at the round table", Stem Cells and Development, 2010, 19(2):143-154.
PCT International Preliminary Report of Patentibility for PCT Patent Application PCT/US2013/064146, dated Sep. 25, 2014.
PCT International Search Report and Written Opinion for PCT Appl. PCT/US13/63736, dated Aug. 12, 2014.
Ennis W., et al. "Clinical experience with a novel regenerative template for hard to heal wounds." In SAWC Annual Spring Meeting; Atlanta, GA. 2012.
Extended European Search Report dated Dec. 2, 2014, for European Patent Application No. EP 12746721.
Faulk W.P., et al. "Human amnion as an adjunct in wound healing." Lancet 1980, 1:1156-1158.
Forbes J, et al., "Dehydrated amniotic membrane allografts for the treatment of chronic wounds: a case series." Journal of Wound Care 2012, 21:290, 292, 294-296.
Gruss J.S., et al. "Human amniotic membrane: a versatile wound dressing." Canadian Medical Association journal 1978, 118:1237-1246.
Hao, Y., et al., "Identification of antiangiogenic and antiinflammatory proteins in human amniotic membrane." Cornea 2000, 19:348-352.
International Preliminary Report of Patentability dated Feb. 17, 2015 for PCT Application No. PCT/US2013/054320.
International Preliminary Report of Patentability for PCT Application No. PCT/US14/28975 dated Feb. 6, 2015.
International Preliminary Report on Patentability dated Dec. 30, 2014, for International Patent Application No. PCT/US2013/063736.
International Preliminary Report on Patentability dated Dec. 8, 2014, for International Patent Application No. PCT/US2013/054322.

(56) References Cited

OTHER PUBLICATIONS

International Preliminary Report on Patentability dated Feb. 14, 2013 for PCT Patent Application No. PCT/US2012/024814.
International Preliminary Report on Patentability dated Nov. 28, 2014, for International Patent Application No. PCT/US2013/054319.
International Preliminary Report on Patentabilty dated Nov. 27, 2014, for International Patent Application No. PCT/US2013/055003.
International Preliminary Report on Patentibility dated Dec. 8, 2014, for International Patent Application No. PCT/US2013/054325.
International Search Report and Written Opinion for PCT Application No. PCT/US2012/065672, mailed Feb. 8, 2013.
International Search Report and Written Opinion for PCT Patent Application No. PCT/US2012/024814 mailed Aug. 16, 2012.
Koizumi N.J., et al., "Growth factor mRNA and protein in preserved human amniotic membrane." Current eye research 2000, 20:173-177.
Li J., et al., "Angiogenesis in wound repair: angiogenic growth factors and the extracellular matrix." Microscopy research and technique 2003, 60:107-114.
Lopez-Valladares MJ, et al., "Donor age and gestational age influence on growth factor levels in human amniotic membrane." Acta ophthalmologica 2010, 88:e211-216.
PCT International Preliminary Report on Patentability dated Dec. 3, 2014 for PCT Patent Application No. PCT/US2013/067618.
PCT International Preliminary Report on Patentability dated Dec. 30, 2014 for PCT Patent Application No. PCT/US13/67622.
PCT International Preliminary Report on Patentability dated Feb. 14, 2013 for PCT Patent Application No. PCT/US12/24814.
PCT International Preliminary Report on Patentability dated Nov. 10, 2014 for PCT Patent Application No. PCT/US2013/067623.
PCT International Search Report and Written Opinion dated Apr. 13, 2015 for PCT Patent Application No. PCT/US15/12087.
PCT International Search Report and Written Opinion dated Apr. 16, 2014 for PCT Patent Application No. PCT/US13/67622.
PCT International Search Report and Written Opinion dated Apr. 21, 2014 for PCT Patent Application No. PCT/US13/67623.
PCT International Search Report and Written Opinion dated Apr. 22, 2014 for PCT Patent Application No. PCT/US13/67618.
PCT International Search Report and Written Opinion dated Apr. 22, 2014 for PCT Patent Application No. PCT/US13/67620.
PCT International Search Report and Written Opinion dated Aug. 26, 2014 for PCT Patent Application No. PCT/US2014/033346.
PCT International Search Report and Written Opinion dated Dec. 29, 2014 for PCT Patent Application PCT/US2014/053270.
PCT International Search Report and Written Opinion dated Dec. 30, 2014 in PCT Patent Application No. PTC/US2014/054603.
PCT International Search Report and Written Opinion dated Jul. 24, 2014 for PCT Patent Application No. PCT/US2014/028975.
Russo A, et al., "The effects of different preservation processes on the total protein and growth factor content in a new biological product developed from human amniotic membrane." Cell and tissue banking 2012, 13:353-361.
Smiell J.M., et al., "Efficacy and safety of becaplermin (recombinant human platelet-derived growth factor-BB) in patients with nonhealing, lower extremity diabetic ulcers: a combined analysis of four randomized studies." Wound repair and regeneration : official publication of the Wound Healing Society [and] the European Tissue Repair Society 1999, 7:335-346.
Steed D.L., et al. Amnion-derived cellular cytokine solution: a physiological combination of cytokines for wound healing. Eplasty 2008, 8:e18.
Uberti M.G., et al., "Amnion-derived cellular cytokine solution (ACCS) promotes migration of keratinocytes and fibroblasts." Annals of plastic surgery 2010, 64:632-635.
Werner S. et al. "Regulation of wound healing by growth factors and cytokines." Physiological reviews 2003, 83:835-870.
Wieman, T.J., et al.,"Efficacy and safety of a topical gel formulation of recombinant human platelet-derived growth factor-BB (becaplermin) in patients with chronic neuropathic diabetic ulcers. A phase III randomized placebo-controlled double-blind study." Diabetes care 1998, 21:822-827.
U.S. Appl. No. 14/157,444, filed Jan. 16, 2014, Koob, et al.
U.S. Appl. No. 14/157,445, filed Jan. 16, 2014, Koob, et al.
Inokuma et al., CTACK/CCL27 Accelerates Skin Regeneration via Accumulation of Bone Marrow-Derived Keratinocytes, Stem Cells, 2006, 24:2810-2916.
MyBioSource/www.mybiosource.com/prods/Recombinant-Protein/CCL27-CTACK/datasheet.php?products-id-444088> Accessed Jun. 9, 2015.
Nibbs et al., CCL27/Pesky: A Novel Paradigm for Chemokine Function, 2003, Expert Opin. Biol. Ther., 3(1):15-22.
Rennert et al. Stem Cell Recruitment After Injury; Lessons for Regenerative Medicine; Regen Med. Nov. 2012, 7(6): 833-850.
Zaja-Milatovic et al., CXC Chemokines and Their Receptors: A case for a significant Biological Role in Cutaneous Wound Healing, Histol. Histopathol., Nov. 2008, 23(11):1399-1407.

COMPOSITIONS AND METHODS FOR RECRUITING AND LOCALIZING STEM CELLS

CROSS-REFERENCE TO RELATED APPLICATION

This application is a continuation-in-part of U.S. patent application Ser. No. 13/815,873, filed on Mar. 15, 2013, which claims priority of U.S. Provisional Application No. 61/713,352, filed on Oct. 12, 2012. The content of both applications are incorporated by reference in their entireties.

BACKGROUND OF THE INVENTION

1. Field of the Invention

This invention is directed, in part, to compositions for recruiting and/or localizing stem cells. In one embodiment, the stem cell recruitment is to the site of a diseased or injured organ and/or body part such that the stem cell is localized at the site for an extended period of time. Stem cell recruitment and/or localization are achieved by use of a sufficient amount of modified placental tissue. Methods for achieving stem cell recruitment and localization are also provided. In a related aspect, this invention is directed to a novel vacuum dehydration device and use thereof.

2. State of the Art

Heretofore, modified placental tissue has been used to treat a diseased or injured organ. However, such use has been limited by the amount of tissue available and the size of the organ. As a general rule, the minimum amount of modified placental tissue to elicit the desired result has been used. For example, the placental tissue is used as a barrier layer between organs so as to prevent adhesion formation. See, for example, U.S. Patent Application Publication No. 2010/0104539. In such cases, the modified placental tissue successfully provides an exogenous therapeutic effect.

It is well understood that a more successful therapeutic outcome is achieved when the treatment regimen includes not only the exogenous therapeutic effect but also an endogenous therapeutic effect. That is to say that patients who are able to cooperatively couple an exogenous therapeutic agent with their body's own ability to heal itself will achieve a better outcome. One mechanism for endogenous healing is the recruitment and/or localization of stem cells to the injured or diseased organ site. However, such in vivo recruitment and/or localization have been exceptionally difficult to achieve.

SUMMARY OF THE INVENTION

This invention is based, in part, on the discovery that application of a sufficient amount of modified placental tissue proximate to a diseased or injured body part of a patient surprisingly elicits stem cell recruitment and/or localization to the site of the diseased or injured body part. Such a discovery provides for not only an exogenous therapeutic effect provided by the modified placental tissue but also an endogenous therapeutic effect provided by the recruited and/or localized stem cells.

Accordingly, in one aspect of this invention it is provided a composition comprising a sufficient amount of modified placental tissue so as to elicit stem cell recruitment and/or localization in vivo when applied directly to or proximate to an injured or diseased body part.

In another aspect of this invention, it is provided a composition comprising a sufficient amount of modified placental tissue so as to elicit an effective amount of stem cell recruiting factors so as to promote stem cell recruitment and/or localization in vivo when applied directly to or proximate to an injured or diseased body part.

In another aspect, it is provided a method for eliciting stem cell recruitment and/or localization within a biological source comprising stem cells, which method comprises contacting said biological source with a sufficient amount of modified placental tissue under conditions which result in stem cell recruitment and/or localization proximate to the modified placental tissue. In one embodiment, the stem cell recruited is a haematopoietic stem cell (HSC). In another embodiment, the stem cell recruited is a mesenchymal stem cell (MSC). In one preferred embodiment, the biological source is an animal such as a mammal including a human. In another preferred embodiment, the biological source is ex vivo such as umbilical cord blood recovered after birth.

In a related aspect, it is provided an innovative vacuum dehydration device for dehydrating placental tissue with improved properties such as minimal damage to the placental tissue, improved quality of embossment, significantly reduced drying time, and reduced cost associated with production of dehydrated placental tissues. The dehydration device comprises a drying housing defining a drying chamber and defining inflow and outflow apertures; and inside the drying chamber, a porous drying board placed on top of a vacuum table. The drying board has a first surface receiving an object such as a placental tissue to be dehydrated and a second surface opposing to the first surface and attaching to the vacuum table. In some embodiments, the first surface of the drying board is capable of imparting an embossment to the dehydrated placental tissue via one or more features of the surface. In yet another aspect, the present invention relates to further modifying the placental tissue by dehydrating the placental tissue in the vacuum dehydration device.

BRIEF DESCRIPTION OF THE DRAWINGS

The accompanying drawings, which are incorporated in and constitute a part of this specification, illustrate several aspects described below.

DETAILED DESCRIPTION OF THE INVENTION

Figure 1:
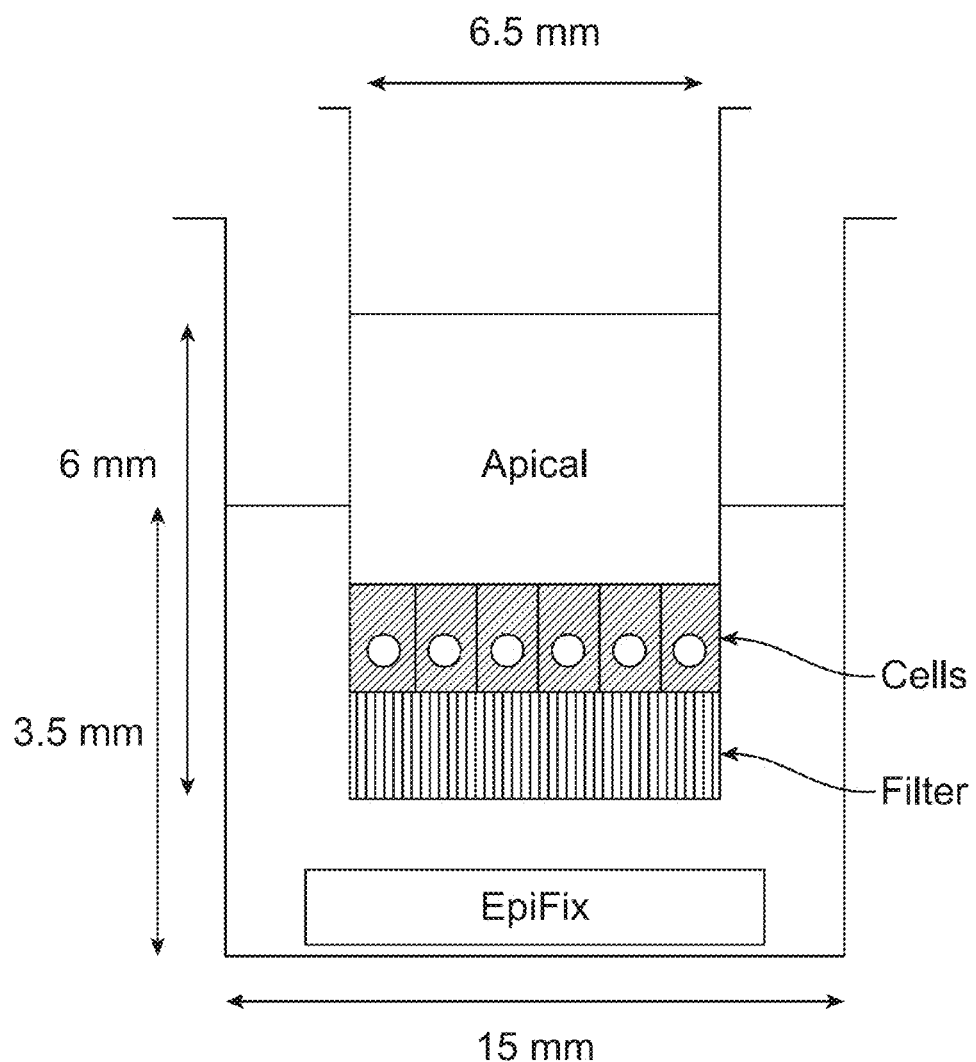
FIG. 1 shows a schematic for a cell culture insert for stem cell migration assays described in Example 3.

Before this invention is disclosed and described, it is to be understood that the aspects described below are not limited to specific compositions, synthetic methods, or uses as such may vary. It is also to be understood that the terminology used herein is for the purpose of describing particular aspects only and is not intended to be limiting.

This invention is predicated in part on the discovery that the use of a sufficient amount of modified placental tissue in treating a diseased or injured body part provides not only an exogenous treatment regimen but surprisingly also promotes an endogenous response which results in stem cell recruitment and/or localization to the body part to be treated.

I. Definitions

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise.

"Optional" or "optionally" means that the subsequently described event or circumstance can or cannot occur, and that the description includes instances where the event or circumstance occurs and instances where it does not. For example, the phrase "optionally cleaning step" means that the cleaning step may or may not be performed.

The term "subject" or "patient" as used herein refers to any vertebrate organism including, but not limited to, mammalian subjects such as humans, farm animals, domesticated pets and the like.

The term "amnion" as used herein includes amniotic membrane where the intermediate tissue layer is intact or has been substantially removed.

The term "body part" as used herein refers to any portion of a body of a subject, including tissue(s) and organs, and also body parts which are not generally referred to as organs provided that such body parts are amenable to treatment with stem cells. Exemplary body parts include, but are not limited to, bone, cartilage, tendon, ligament, retina, peripheral nerve, peripheral nerve sheath, small intestine, large intestine, stomach, skeletal muscle, heart, liver, lung and kidney.

The term "diseased" as used herein refers to an organ and/or body part that is characterized as being in a disease state, or susceptible to being in a disease state, wherein the disease is amenable to treatment with stem cells.

The term "injured" as used herein is used to have an ordinary meaning in the art, and includes any and all types of damage to an organ and/or body part, wherein the injury is amenable to treatment with stem cells.

The term "modified placental tissue" refers to any and all components of placental tissue including whole placental tissue that has been modified by cleaning, disinfecting, and/or segmenting the tissue as well as to separated components of placental tissue such as amnion, chorion, intermediate layer, the umbilical cord, and the like.

Modified tissue may maintain cellular layers, such as the epithelial layer and/or the fibroblast layer. Modified placental tissue may include further modification, such as lamination of one or more layers of placental tissue, micronization of placental tissue, chemisorption or physisorption of small molecules, proteins (e.g. growth factors, antibodies), nucleic acids (e.g. aptamers), polymers, or other substances.

The term "sufficient amount" refers to an amount of a modified placental tissue that is sufficient to provoke stem cell recruitment proximate to or on the modified placental tissue over time, either in vivo or in vitro. The "sufficient amount" of a modified placental tissue will vary depending on a variety of factors, such as but not limited to, the type and/or amount of placental tissue used, the type and/or size of the intended organ and/or body part to be treated, the severity of the disease or injury to the organ and/or body part to be treated and the administration route. The determination of a "sufficient amount" can be made by one of ordinary skill in the art based on the disclosure provided herein.

The term "stem cell recruiting factors" refers to any and all factors that are capable of recruiting stem cells and causing them to migrate towards a source of such factors. Non-limiting examples of stem cell recruiting factors may be one or more CC chemokines, CXC chemokines, C chemokines, or $CX_3C$ chemokines.

The term "stem cell recruitment and/or localization" refers to direct or indirect chemotaxis of stem cells to a body part where a modified placental tissue is applied. The term "recruitment" in the context of the present application refers to migration of stem cells to an injured or diseased organ or body part induced by application of a modified placental tissue encompassed by this invention.

The recruitment may be direct, wherein stem cell recruiting factors (e.g. chemokines, which induce cell chemotaxis) in a modified placental tissue are released from the placental tissue and induce stem cells to migrate towards the body part where a modified placental tissue is applied. In one aspect, the recruitment may be indirect, wherein stem cell recruiting factors in a modified placental tissue are released from the placental tissue which induce nearby cells to release factors (e.g. chemokines), that in turn induce stem cells to migrate towards the body part where a modified placental tissue is applied. Furthermore, stem cell recruitment may embody both direct and indirect factors.

The term "localization" means that the recruited stem cells remain for a prolonged period of time at the injured or diseased organ or body part where the modified tissue is applied. Localization is achieved by the presence of the modified placental tissue and/or other agents facilitating the localization, such as agents for increasing viscosity, and thixotropic agents, as detailed in various embodiments below.

The stem cells which can be localized or recruited can be endogenous stem cells already present in the patient. Alternatively, the stem cells can be from an exogenous source and administered adjacent to a diseased or injured site in the patient. In either case, the modified placental tissue acts to retain those stem cells already proximate thereto so as to localize those stem cells while at the same time recruiting stem cells more distant thereto to migrate to the diseased or injured site.

The term "proximate to" as used herein means adjacent to, or on a body part. For example, modified placental tissue proximate to the heart means that the placental tissue may be on the heart, or within 1-2 cm of the heart, but still close enough to exert a stem cell recruiting effect. In general, "proximate to" means that the modified placental tissue is placed sufficiently close so as to recruit stem cells to the diseased or injured organ and/or body part. Such a distance is generally determined by one of ordinary skill in the art but preferably is within about 5 cm, within about 4 cm, within about 3 cm, within about 2 cm, or within about 1 cm, of an organ or body part.

The term "exogenous" refers to non-naturally occurring substances, including allograft tissue, such as modified placental tissue, and stem cells. In the context of the present invention, an exogenous therapeutic effect refers to a therapeutic effect produced by a modified placental tissue, when applied to an injured or diseased organ or body part, for example, functions as a physical barrier between organs or body parts to prevent adhesion formation.

The term "endogenous" refers to autologous biological substances from a subject. In the context of the present invention, an endogenous therapeutic effect is achieved when the body of the treated subject produces an autologous response to the treatment. For example, the stem cells are recruited and/or localized at the site where a modified placental tissue is applied as an autologous response produced by the body of the treated subject.

The term "biological source" refers to an organ or tissue that contains a population of stem cells available to be recruited, e.g. bone marrow. The biological source may be in vivo or in vitro.

II. Modification of Placental Tissue

In one embodiment, placental tissue may be modified as described in U.S. Ser. No. 61/683,698, including cleaning, separation of the amnion and chorion, removal or maintenance of the epithelial cell layer, decontamination, and dehydration. Dehydration may be accomplished using the drying apparatus as described in U.S. Ser. No. 61/683,700. Both of which applications are incorporated herein by reference in their entirety. Each aspect of that process produces modified placental tissue for the purposes of this invention whether used alone or in combination. However, it is preferred that the modified placental tissue include at least the steps of cleaning and decontamination. As such, modified placental tissue preferably comprises placental tissue which has been cleaned and decontaminated and also includes placental tissue which has undergone one or more of separation of the amnion and chorion, removal of the epithelial cell layer, and dehydration.

In some embodiments, the modified placental tissue is selected from amnion, chorion, or both amnion and chorion. In one embodiment, modified placental tissue includes the umbilical cord and in another embodiment, it does not.

Modified placental tissue can also be formed into layers which may be dried separately and laminated together or dried together to form multi-layer laminates. In one embodiment, two or more amnion layers are laminated. In another embodiment, two or more chorion layers are laminated. In yet another embodiment, amnion layer(s) and chorion layer(s) are laminated. Optionally, before lamination, the amnion layer is further modified to substantially remove the epithelial layer. Preferably, the fibroblast layer remains substantially intact after removal of the epithelial layer.

Modified placental tissue may also be micronized into particles of a variety of sizes. Micronized placental tissue may be sandwiched between one or more layers of a multi-layer laminate, or on top of a laminate. Micronized placental tissue may also be added to single layer of modified placental tissue. See, for example, U.S. Provisional Application Ser. No. 61/543,995 which is incorporated herein by reference in its entirety.

Modified placental tissue may be further processed to obtain an extract of biological factors in an aqueous solution. Making and using such an extract is described in U.S. patent application Ser. No. 13/744,331, which is incorporated herein by reference in its entirety.

In certain embodiments, the modified placental tissue described herein is dehydrated using an innovative dehydration device which modifies the drying apparatus as described in U.S. patent application Ser. No. 13/744,332, which is incorporated herein by reference in its entirety, by the inclusion of a functional drying board in contact with a self-integrated vacuum source. More specifically, the dehydration device comprises: (i) a drying housing defining a drying chamber and defining inflow and outflow apertures; and (ii) inside the drying chamber, a porous drying board placed on top of a vacuum table. The porous drying board has a first surface which receives the placental tissue to be dehydrated; and a second surface opposing the first surface, which second surface is in direct or indirect contact with the vacuum table. In such a configuration, the dehydration device allows vacuum suction to hold in place the placental tissue placed on the surface of the drying board during the dehydration process.

In certain embodiments, the drying board is made of materials that allow just sufficient adhesion of the placental tissue to the surface such that the placental tissue is firmly held stretched during the drying process to prevent the placental tissue from movement and/or shrinkage. On the other hand, overly adhesive material would make it difficult to remove the dehydrated placental tissue from the surface, thereby causing undesirable tearing or other damages to the dehydrated placental tissue. Preferably, the material for the drying board has a hydrophobic surface and a desired elasticity. In one embodiment, the material for the drying board is silicone or polycarbonate. Preferably, the drying board comprises a polycarbonate insert which is surrounded entirely by silicone to provide the desirable stiffness and the hydrophobic property. More preferably, the drying board has a thickness of at least ⅛ inch, at least ¼ inch, at least ⅜ inch, at least ½ inch, at least ⅝ inch, at least ¾ inch, at least ⅞ inch, or at least 1 inch to provide a desirable stiffness thereby preventing flexing/bending during vacuum drying.

It is within the purview of one of ordinary skill in the art to select a material of appropriate stiffness for the drying board. For example, a stainless steel drying board may be used. When such material is used, a specialized surface treatment or coating is applied to the drying board to facilitate handling of the wet placental tissue as well as separating dehydrated placental tissue to avoid damages. Such coating material includes, but is not limited to, polycarbonate and polytetrafluoroethylene (PTFE). Additional coating material can be a hydrogel such as poly(N-isopropyl acrylamide), which is capable of changing the surface properties from hydrophilic to hydrophobic with a temperature change, e.g., to about 32° C. In this way, controlled adhesion of placental tissue to the drying board can be achieved by adjusting the temperature.

The drying board may be further improved to have other desirable features. For example, the drying board contains indentation, protrusion, or both to create an embossment onto the tissue graft. The drying board has a positive or negative embossment such that the embossment is imposed onto the placental tissue during the drying process. Exemplary embossments include, but are not limited to, letters, characters, designs, logos, pictures, patterns, etc. Preferably, the embossment imposed on the placental tissue allows an end user to easily distinguish by naked eyes one side from the other side of the dehydrated placental tissue, for example, by way of an asymmetrical feature that appears differently when visualized from one side than from the other side.

In some embodiments, the drying board may be translucent or opaque. Preferably, the drying board has a color that contrasts the natural color of the placental tissue and makes visual inspection of the placental tissue, when placed on the board, easy, such as a mint green or medical blue color. In some embodiments, the drying board has a smooth surface. In other embodiments, the drying board has a textured surface. In yet other embodiments, the drying board has a combination of areas of smooth surface and areas of textured surface such that the drying board imparts a "watermark" on to the dehydrated placental tissue. One skilled in the art would be able to vary the texture of the surface of the drying board in contact with the placental tissue to obtain a dehydrated placental tissue having the desired texture.

The drying board is porous, having holes or perforation spread out the entire area of the drying board to allow the application of vacuum pressure. Once the placental tissue is placed on the surface of the drying board, vacuum suction is applied to press the placental tissue onto the drying surface of the board. The pressure of the vacuum is adjusted such that the embossment is clearly imposed onto the placental tissue while preventing the placental tissue and the board from bending, flexing, and/or shrinking.

The number and the size of the holes can be varied to achieve the desirable results. In some embodiments, the holes may be arranged in a desirable pattern. Preferably, the holes spread evenly on the entire surface of the board such that all the holes are covered by the placental tissue to provide even and consistent vacuum pressure. The pattern of the holes may or may not be of symmetrical design. Preferably, the holes are arranged in a square-shaped symmetrical pattern. More specifically, the geometry of the holes may include letters and/or other designs or artwork. The holes could also have a changing geometry through the thickness of the drying board. For example, a hole having a 5 mm diameter and 1 mm depth may be immediately next to a hole having a 1 mm diameter and 0.1 mm depth such that the embossment to the placental tissue has a particular design by controlling the depth and size of the holes. It is within the purview of one skilled artisan to balance the needs for varying the number, diameter and depth of the holes to achieved not only the desirable design but also a consistent, desirable vacuum pressure.

In one embodiment, there are about 50, about 100, about 150, about 200, about 250, about 300 holes over an area of about 100 cm$^2$, about 150 cm$^2$, about 200 cm$^2$, about 250 cm$^2$, about 300 cm$^2$, about 350 cm$^2$, about 400 cm$^2$, about 450 cm$^2$, or about 500 cm$^2$. In another embodiment, the size of the holes may range from 0.1 mm to 10 mm in diameter, for example, less than 0.1 mm, less than 0.5 mm, less than 1 mm, less than 2 mm, less than 3 mm, less than 4 mm, less than 5 mm, less than 6 mm, less than 7 mm, less than 8 mm, less than 9 mm, or less than 10 mm. Preferably, the size of the holes is between 4 mm and 8 mm in diameter. The holes on the drying board may or may not be of the same size. The number of holes and the size of the holes may be varied to achieve a desirable result. For example, the number of the holes can be less than 50 or greater than 300; and the diameter of the holes may be less than 0.1 mm or greater than 10 mm.

The general principle is the greater the number of the holes, the smaller the size of the holes. The number and size of the holes can be determined by routine experimentation following the disclosure of this invention.

The vacuum source supplies reduced pressure to the vacuum table placed within the drying chamber. The vacuum table and by extension, the drying board and the placental tissue are then subjected to variable and controllable amounts of reduced pressure from the vacuum source to exert mechanical force on the placental tissue thereby holding the placental tissue in place. It is within the purview of one skilled artisan to adjust the vacuum pressure such that a minimal pressure is applied to the placental tissue to avoid damages to the tissue; whereas the vacuum pressure is sufficient to prevent the placental tissue from moving and/or shrinking during the drying process and to impose a clear embossment to the placental tissue.

When dehydration is performed at a vacuum pressure that is too high, a tissue graft with uneven surface, such as "bubble" formation, is produced; when dehydration is performed at a vacuum pressure that is too low, the placental tissue is insufficiently stabilized during the process and as a result, the tissue may shrink, wrinkle, and/or have a blurred embossment.

Accordingly, one skilled in the art would understand that the dehydration device is controlled by a differential pressure gradient developing from the difference between the slight positive pressure of the circulated airflow through the chamber plenums and the slight negative pressure from the vacuum applied to the graft by the inner channels of the drying fixture. This gradient can be calculated according to the formulation below and manipulated to facilitate tissue and to expedite drying through the design features of this vacuum drying apparatus. This is accomplished by the control of at least four parameters, namely the number of contacting holes on the board surface, the size or diameter of the holes, vacuum pressure, and the total surface area of the drying board.

$$F = Pv \times Ah/Ab$$

where F is the holding pressure; Pv is the vacuum pressure, Ah is the sum of the holes surface area (throughout the board) at the interface with the placental tissue; and Ab is the surface area of the board.

In case when the circular cross section holes have the same size, the formula below may be used:

$$Ah = Pi \times R2 \times N$$

where Pi is the vacuum pressure, R2 is the square radius of a hole; and N is the number of the holes throughout the board.

Selection of a suitable vacuum table is within the purview of one skilled in the art. A number of commercially available vacuum tables are suitable for the purpose of this invention. For example, vacuum tables may be obtained from Systematic Automations.

In some embodiments, the drying board is heated to a temperature that is sufficiently high to accelerate the drying process but not too high to damage the placental tissue. Alternatively, the air traveling thru the plenums in the drying chamber is heated to a constant temperature between 20° C. and 45° C. Preferably the temperature of the air or the board or both is held constant at 45° C. to decrease the moisture content in the drying chamber to speed up the drying process. The heated air is filtered and circulated throughout the drying chamber to remove moisture from the placental tissue and the atmosphere inside the chamber. In still other embodiments, moisture is removed from the airflow by placing a desiccant in-line to one or both of the airflow inlet and outlet lines, yet exterior to the chamber. Recirculating the heated air through a desiccant further reduces the cost and accelerates the drying process. Preferably, the heated air flow is in an angle of 45° relative to the surface of the placental tissue.

In other aspects, multiple placental tissue grafts can be placed onto the drying board to dry more than one placental tissue graft in the dehydration device at the same time. Although the dehydration device is useful in dehydrating the tissue grafts described herein, it can be used for dehydrating objects other than placental tissue.

III. Use of Modified Placental Tissue

Inventors of the present application surprisingly discovered that the use of the modified placental tissue encompassed by this invention achieved a two-fold therapeutic effect: application of the modified placental tissue to an injured or diseased organ or body part of a subject not only produces an exogenous therapeutic effect but also an endogenous therapeutic effect provided by recruitment and/or localization of stem cells to the site of application.

It was unexpectedly discovered that upon application of a modified placental tissue to an injured or diseased organ or body part, the stem cells migrate to the injured or the diseased site such that the stem cells accumulate at the site at a higher concentration than the concentration of the stem cells under a normal physiological condition. This recruitment of stem cells is directly induced by the modified placental tissue applied to the site, which releases stem cell recruiting factors such as chemokines upon application. Alternatively, the recruitment of stem cells is indirectly induced by the modified placental tissue applied to the site—application of the modified placental tissue has an inducing effect on the nearby cells, which in turn release stem cell recruiting factors to attract stem cells to the injured or diseased site. In preferred embodiments, the stem cells recruitment is induced by a combination of direct and indirect effects exercised by the modified placental tissue.

In some aspects, one or more stem cell recruiting factors that enhance stem cell chemotaxis and/or recruitment may be added to modified placental tissue, including the micronized placental tissue or an extract or aqueous solution of modified placental tissue, of the present technology. Alternatively, stem cell recruiting factors may be added to layers of a laminate tissue graft. Thus, for example, cytokines, chemokines, growth factors, extracellular matrix components and other bioactive materials can be added to the modified placental tissue to enhance native stem cell recruitment. Specific non-limiting examples of stem cell recruiting factors may include one or more of the following: CC chemokines, CXC chemokines, C chemokines, or $CX_3C$ chemokines. Other stem cell recruiting factors may further include growth factors such as cc-Fibroblast Growth Factor ($\alpha$FGF or $\alpha$FGF-1), $\beta$-Fibroblast Growth Factor ($\beta$FGF-1 or $\beta$FGF-2), Platelet-Derived Growth Factor (PDGF), Vascular Endothelial Growth Factor (VEGF-A, B, C, D or E), Angiopoietin-1 and -2, Insulin-like Growth Factor (IGF-1), Bone Morphogenic Protein (BMP-2 and -7), Transforming Growth Factor-$\alpha$ and -$\beta$ (TGF-$\alpha$ and TGF-$\beta$) Epidermal Growth Factor (EGF), Connective Tissue Growth Factor (CTGF), Hepatocyte Growth Factor (HGF), Human Growth Hormone (HGH), Keratinocyte Growth Factor (KGF), Tumor Necrosis Factor-$\alpha$ (TNF-$\alpha$), Leukemia Inhibitory Factor (LIF), Nerve Growth Factor (NGF), Stromal cell derived factor 1 (SDF-1$\alpha$), Granulocyte Macrophage Colony Stimulating Factor (GM-CSF) and other factors as is known in the art.

Once the stem cells are recruited to the injured or diseased organ or body part, the therapeutic effect is enhanced by localization of the stem cells at the site for a prolonged period of time. Localization of the stem cells is achieved by the presence of a modified placental tissue, which continuously releases stem cells recruiting factors over an extended period of time. Thus, it is within the purview of one of ordinary skill in the art to further modify the placental tissue to incorporate different phases of release of the stem cell recruitment factors. For instance, micronized placental tissue is used in combination with modified placental tissue to achieve immediate, delayed, and extended release of the stem cell recruitment factors. In another embodiment, an extract or aqueous solution of the modified placental tissue is combined with other forms of modified placental tissue such that the extract or solution can elicit immediate recruitment of stem cells by the fast onset release of stem cell recruiting factors; while other forms of modified placental tissue have delayed release of stem cell recruiting factors such that the stem cells are recruited to and/or localized at the site for an extended period of time, thereby enhancing the therapeutic effects.

Additional agents may be co-administered to the injured or diseased organ or body part along with the modified placental tissue to facilitate localization of the stem cells recruited to the site. For instance, the modified placental tissue may be co-administered with an agent to increase the viscosity at the local site. Any thickening agents, including gelling agents, thixotropic agents, phase changing agents, etc., that are suitable for pharmaceutical use is within the scope of this invention. When co-delivered with the modified placental tissue, these agents form a viscous or gel-like bioerodable or biodegradable mass in vivo which limits transport away from the site of delivery and allows for the diffusion of the stem cell recruiting factors from the mass formed over a period of time.

The biocompatible thixotropic agent is selected, by way of example only, from hyaluronic acid, collagen, thrombin gels, fibrin gels and fibrin glues. In another embodiment, the phase changing agent is a gel forming agent, such as a Pluronic® (e.g., a copolymer of oxyethylene and oxypropylene). Preferably, any polymer used as a gelling agent, a thixotropic agent or a phase changing agent is bioerodible. In yet another embodiment, the organ or body part is selected from the group consisting of skin, mucosal membrane, gum adjacent to teeth, bone, cartilage, tendon, retina, peripheral nerve, peripheral nerve sheath, small intestine, large intestine, stomach, skeletal muscle, heart, liver, lung, and kidney.

In other embodiments, a thixotropic composition or a phase-changing composition is formed before delivering to a subject. Such compositions comprise a modified placental tissue and a thickening agent. A thixotropic composition is one where in the absence of shear, the composition has high viscosity (it does not move) and in the presence of shear, the composition's viscosity is greatly reduced so as to be deliverable under shear. An example of a thixotropic composition is toothpaste. A phase-changing composition is an aqueous composition which undergoes a change from a liquid to a gel or solid mass based on a suitable trigger such as an increase in temperature, light activation, electromagnetic stimulation, the addition of a phase-changing co-factor (e.g., alginates plus calcium). Such compositions are well known in the art. These compositions are preferably deliverable under injection but also can be delivered topically as necessary. If the viscosity of the composition does not permit conventional injection, high pressure syringes can be used and are well known in the art. Non-limiting examples of such high pressure syringes include those described in U.S. Pat. No. 6,503, 244 (incorporated herein by reference in its entirety) and the like.

Thus, a number of therapies entailing the application of a modified placental tissue to an injured or diseased organ or body part result in an endogenous therapeutic effect by way of recruitment and/or localization of stem cells in addition to an exogenous therapeutic effect. Such therapies are exemplified below in a way not intended to limit this invention. Additional exemplary therapies are described in U.S. patent application Ser. Nos. 13/815,873 and 61/713,352, which are specifically incorporated herein by reference.

A. Wound Healing

For example, a modified placental tissue has been used in numerous wound healing applications. Amnion contains growth factors such as EGF, bFGF, and PDGF that promotes wound healing and re-epithelialization. This invention is based on the discovery that when used in sufficient amounts, such modified placental tissue also induces, directly or indirectly, stem cell recruitment proximate to the site of application. In one aspect, the application of the modified placental tissue described herein where the epithelial layer of the skin is disrupted can be effective in delivering the growth factors directly to the injured site to promote healing as well as stem cell recruitment. Amnion is a unique ECM due to the presence of collagen types IV, V and VII, which enables the amnion to bind water and swell. It is understood that the wound healing aspect of the modified placental tissue has an exogenous therapeutic effect whereas the stem cell recruitment arising directly and/or indirectly from the modified placental tissue has an endogenous therapeutic effect.

Similarly, the intermediate tissue layer of the placental tissue is composed largely of glycoproteins and proteoglycans, which also enables the intermediate tissue layer to bind water. Thus, the modified placental tissue when applied to a diseased or injured organ or body part helps retain water at that site, which facilitates healing. For example, cell migration, including stem cell recruitment, within the healing cascade is facilitated in a hydrophilic environment. The intermediate layer is also composed of collagen types I, III, and IV. Type I collagen provides mechanical strength to skin by providing a major biomechanical scaffold for cell attachment and anchorage of macromolecules. Type III collagen provides elasticity.

The types of wounds that present themselves to physicians on a daily bases are diverse. Acute wounds are caused by surgical intervention, trauma and burns. Chronic wounds are wounds that are delayed in closing compared to healing in an otherwise healthy individual. Examples of chronic wound types plaguing patients include diabetic foot ulcers, venous leg ulcers, pressure ulcers, arterial ulcers, and surgical wounds that become infected.

The physician's goal when treating traumatic wounds is to heal the wound while allowing the patient to retain natural function in the area of the wound with minimal scaring and infection. If a wound becomes infected, it can lead to a loss of limb or life. For the most part, physicians heal these patients without incident. However, physicians dealing with chronic wounds are mainly concerned with closing the wound as quickly as possible to minimize the risk of an infection that could lead to loss of limb or life. Chronic wounds are wounds on patients that have co-morbidities that complicate or delay the healing cascade. In one aspect, the modified placental tissue described herein can function as a tissue regeneration template that delivers essential wound healing factors, extracellular matrix proteins, inflammatory mediators as well as elicit stem cell recruitment and/or localization to that site to help reduce inflammation, enhance healing, and reduces scar tissue formation. In this aspect, the modified placental tissue including micronized placental tissue described herein are used in treating wounds amenable to negative pressure technology, including burns and ulcers, such as chronic ulcers, diabetic ulcers, decubitus ulcers and the like. In another aspect, the modified placental tissue is used in conjunction with conventional treatments, including, but not limited to, negative pressure therapy, and may also be used in combination with matrices or scaffolds comprised of biocompatible materials, such as collagen, hyaluronic acid, gelatin or combinations thereof.

B. Preventing Scar Formation

In another aspect, the modified placental tissue described herein can be used to prevent scar formation as a result of a surgical incision. The modified placental tissue is very useful where large incisions are produced by a surgical procedure. Particularly, the modified placental tissue is useful for addressing or alleviating complications to the spine and surrounding regions that occur after surgery. In one aspect, the modified placental tissue is useful in preventing or reducing scar formation on the spine or near the spine and sealing dural tears. Scar formation at or near the spine after surgery can be very debilitating and possibly require subsequent operations to address the symptoms as discussed above. The term "anti-adhesion" is also used in the art to refer to the prevention of scar tissue at or near the spine. As an exogenous therapy, the modified placental tissue can be used as a protective barrier to protect the spinal dura from post-surgical trauma from the surrounding surgical site. For example, the composition can prevent damage to the spinal dura caused by sharp edges from newly cut bone such as vertebrae. In other aspects, the modified placental tissue can be used for anterior lumbar interbody fusion, posterior lumbar interbody fusion trans-lumbar interbody fusion, anterior cervical discectomy and fusion, micro discectomy, spinal dura repair, and as a dura sealant to prevent CSF leakage. In each aspect, application of the modified placental tissue to the site induces autologous response by recruiting and/or localizing stem cells from other parts of the body to the site, thereby enhancing the therapeutic effects.

C. Orthopedic Applications

In other aspects, the modified placental tissue described herein can be used in orthopedic applications (i.e., sports medicine). Sports medicine includes the repair and reconstruction of various soft-tissue injuries in or around joints caused by traumas, or chronic conditions brought about by repeated motion, in active individuals and athletes. For example, sports medicine includes the treatment of a variety of different injuries associated with, but not limited to, shoulders, elbows, feet, ankles hand and wrists. In one aspect, the modified placental tissue can be used to alleviate inflammation (e.g., tennis elbow, carpel tunnel, etc.). In other aspects, the modified placental tissue can be applied to articular surfaces in order to provide medical benefits. For example, the modified placental tissue can help reduce inflammation or swelling of an articular surface. In other aspects, the modified placental tissue can help repair and/or regrow chondrocytes. In further aspects, the modified placental tissue described herein can be used in other orthopedic applications such as aid in the repair of periostium; help repair ruptured/damaged bursa; help secure void filling material during bone repair; or in applications involving a subject's extremities (e.g., anti-adhesion barrier for small bone fixation, anti-adhesion barrier where metal plating or hardware is used, or help repair ruptured/damaged bursa). In each case, the additional benefit of stem cell recruitment and/or localization provides a further level of endogenous therapy to the diseased and/or injured organ and/or body part.

D. Other Therapies

In other aspects, the modified placental tissue can be used to reduce inflammation related to gingivitis, periodontitis, mucositis, and peri-implantitis, treatment of periodontal intra-bony defects to regenerate new bone, tissue/organ repair and regeneration, periodontal ligament, and cementum, regenerate lost bone around dental implants, increase the amount of clinical attachment following osseous contouring, treatment of gingival recession, regeneration of interdental papilla, either through surgical reconstruction or by directly injecting the papilla to increase size and thickness, applied over the top of a barrier membrane or biocompatible mesh in alveolar vertical and horizontal bone augmentations, applied over the surgical site after primary closure to aid in healing, applied onto autograft, xenograft, alloplast, caderivic allograft or placental allograft soft tissue graft, either before, during, or after placement of the soft tissue graft in the treatment of gingival recession, increasing the amount of clinical attachment, gingival augmentations around teeth and dental implants, expanding the zone of keratinized tissue, thickening overlying gingival tissue in guided bone regeneration, mixed with a alloplast, xenograft, and or caderivic bone graft, either before, during, or after placement for use in the treatment of intrabony defects to regenerate new bone, periodontal ligament, and cementum, in guided bone regeneration regenerate lost bone around implants, site preservation, fenestration and dehiscence defects, primary and secondary alveolar ridge augmentations, sinus elevations, and gingival flap perforations. In applications involving dentin and pulpal tissue, reduce inflammation of pulpal tissue, treatment of endodontic lesions, pulpal regeneration, and injected into hollowed pulpal chamber prior to obturation in endodontic therapy. In applications involving oral mucosa tissue to reduce inflammation in oral lesions, the treatment of oral lesions, and applied onto autograft, xenograft, alloplast, caderivic allograft or placental allograft soft tissue graft either before, during, or after placement of the soft tissue graft to replace larger amounts of mucosal tissue lost through disease or traumatic injury.

In each application described above, the modified placental tissue is applied directly to, proximal to, or internal to a diseased and/or injured body part in an amount sufficient to attract stem cells and promote endogenous healing. In various aspects, in order to attract stem cells to a damaged body part, a sufficient amount of placental tissue is required before the stem cells migrate to the target body part. For example, as described in Example 3, stem cells migration occurred in response to EpiFix® in a concentration-dependant manner. A 1.5 mm diameter disk of EpiFix® modified placental tissue was found not to result in a significant migration of stem cells in vitro. However, 4 mm diameter EpiFix® modified placental tissue disks and 12×13 mm square EpiFix® patches show a statistically significant increase in migration of stem cells compared with control cells. One square centimeter of EpiFix® weighs 4 mg. Surprisingly, stem cell migration even in vitro requires a minimum mass of modified placental tissue to induce migration, i.e. more than the mass of a 1.5 mm disk of EpiFix® modified placental tissue. Stated another way, the presence of a sufficient amount of modified placental tissue correlates to a sufficient concentration of stem cell recruiting factors such that stem cell recruitment and/or localization are achieved.

In addition, Example 4 describes in vivo implantation of a 5×5 mm square EpiFix® modified placental tissue patch, leading to a statistically significant increase in stem cell recruitment in mice, starting at about 2 weeks post-implantation. In this regard, it is contemplated that the use of a larger amount of EpiFix® modified placental tissue would further enhance stem cell recruitment either in a reduced time frame to achieve stem cell recruitment and/or the number of stem cells recruited over a given period of time. In various embodiments, the enhancement of stem cell recruitment is at least 5%, 10%, 20%, 30%, 40%, 50%, 60%, 70%, 90%, 100% or more, when compared to the subject not receiving a modified placental tissue. Regardless, in at least this example, the data shows that more than a minimal amount of EpiFix® modified placental tissue is required in order to effect stem cell recruitment and/or localization.

Further, it is also contemplated that micronized modified placental tissue can enhance the rate of stem cell recruitment in a particular body part. In these aspects, micronized modified placental tissue is added to modified placental tissue, either a single layer of modified placental tissue, or in between a multi-layer laminate of placental tissue.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Preparation of Micronized Placental Tissue

Amnion/chorion tissue grafts used here to produce the micronized particles were produced by the process described in US 2008/0046095, which is incorporated by reference in its entirety. Tissue grafts (4 cm×3 cm) and two 9.5 mm steel grinding balls were placed in 50 mL vials and the vials subsequently sealed. The vials were placed in the Cryo-block, and the Cryo-block was placed in a Cryo-rack. The Cryo-rack was placed into a liquid nitrogen holding-Dewar flask. Tissue samples were subjected to vapor phase cooling for no more than 30-60 minutes. The Cryo-rack was removed from the Dewar flask, and the Cryo-block was removed from the Cryo-rack. The Cryo-block was placed into the Grinder (SPEX Sample Prep GenoGrinder 2010) and set at 1,500 rpm for 20 minutes. After 20 minutes had elapsed, the tissue was inspected to ensure micronization. If necessary, the tissue was placed back into the Dewar flask for an additional 30-60 minutes, and moved to the grinder for an additional 20 minutes to ensure sufficient micronization. Once the tissue was sufficiently micronized it was sorted using a series of American Standard ASTM sieves. The sieves were placed in the following order: 355 µm, 300 µm, 250 µm, 150 µm, and 125 µm. The micronized material was transferred from the 50 mL vials to the 355 µm sieve. Each sieve was agitated individually in order to thoroughly separate the micronized particles. Once the micronized particles were effectively separated using the sieves, the micronized particles having particle sizes of 355 µm, 300 µm, 250 µm, 150 µm, and 125 µm were collected in separate vials.

Example 2

Preparation of Tissue Grafts with Micronized Placental Tissue

Various modifications and variations can be made to the compounds, compositions and methods described herein.

Other aspects of the compounds, compositions and methods described herein will be apparent from consideration of the specification and practice of the compounds, compositions and methods disclosed herein. It is intended that the specification and examples be considered as exemplary.

A detailed description of suitable cross-linking agents and procedures is provided in concurrently filed U.S. Patent Application Ser. No. 61/683,697 and entitled PLACENTAL TISSUE GRAFTS MODIFIED WITH A CROSS-LINKING AGENT AND METHODS OF MAKING AND USING THE SAME which application is incorporated herein by reference in its entirety.

A detailed description of reinforced placental tissue grafts is provided in concurrently filed U.S. Patent Application Ser. No. 61/683,699 and entitled REINFORCED PLACENTAL TISSUE GRAFTS AND METHODS OF MAKING AND USING THE SAME which application is incorporated herein by reference in its entirety.

A detailed description of making and using micronized placental tissue and extracts thereof is provided in concurrently filed U.S. Patent Application Ser. No. 61/683,700 and entitled MICRONIZED PLACENTAL TISSUE COMPOSITIONS AND METHODS OF MAKING AND USING THE SAME which application is incorporated herein by reference in its entirety.

Example 3

Cell Migration in the presence of EpiFix®

Human mesenchymal stem cells (human Msc) were evaluated in cell culture in the presence of samples of EpiFix® to determine whether the EpiFix® would induce migration of the human MSC. EpiFix® is a layer of amnion and chorion with the epithelial layer intact.

Materials and Methods

Standard migration assays were performed in 24-well cell culture inserts with 8-μm pore membrane filters at the bottom of the insert (see FIG. 1; BD Biosciences). 24 hours prior to the start of the experiment, human MSCs (one donor, passage 3) were cultured in serum free media, and 300 μL of 5 μg/mL fibronectin in PBS was placed into each cell culture insert to enable adsorption of fibronectin to the cell culture insert surface overnight.

Figure 2:
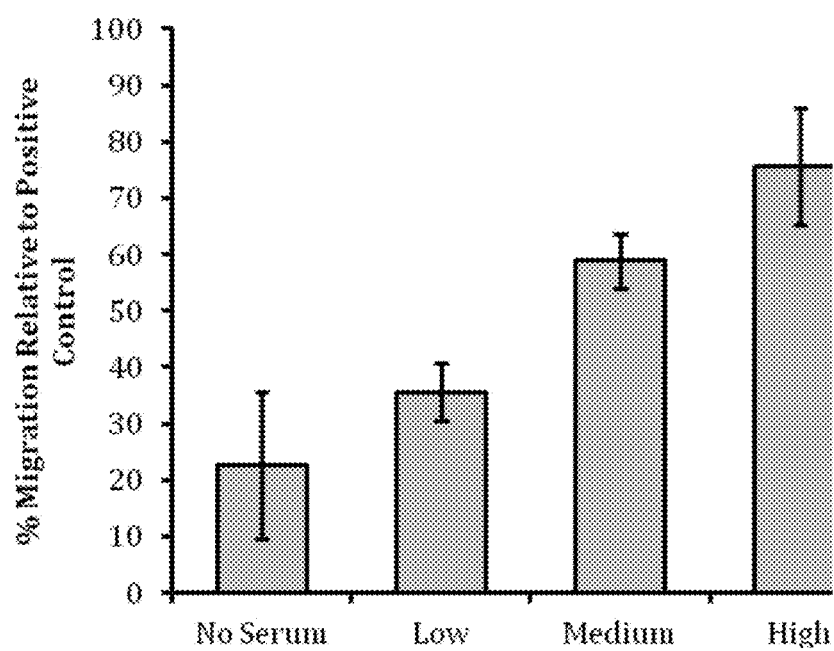
FIG. 2 shows a bar graph of percent cell migration in human mesenchymal stem cells (MSCs) cultured in the presence of various amounts of EpiFix®. Details are described in Example 3.

On the day of the experiment, 700 μL of serum-free culture medium was loaded into the bottom wells of the plate, followed by the addition of differently sized portions of sterilized EpiFix® (Low: 1.5-mm diameter disk; Medium: 4-mm diameter disk; High: 12×13 mm square, trimmed into 3-4 mm square pieces; n=6 EpiFix® tissue donors tested) (FIG. 2). One square centimeter of EpiFix® weighs 4 mg. Serum-free medium and medium with 10% fetal bovine serum (n=6) acted as negative and positive controls, respectively. Human MSCs (40,000 cells in 300 μL) were then loaded into the cell culture inserts and cultured for 24 hours. Then, both sides of the cell culture inserts were rinsed with PBS, and non-migrating cells in the upper portion insert were removed with a cotton-tipped applicator. Cells on the lower side of the insert plus the membrane filter were fixed in 10% formalin for 20 minutes, then rinsed and stained with hematoxylin for 5 min. The number of cells migrating through the membrane were counted on the lower surface of the membrane with an inverted microscope (Nikon TE2000; SPOT Software 4.6).

Data were normalized to the 10% FBS positive control and are expressed as mean±standard deviation of counted, migrated cells per 100× field micrograph for each sample well. Statistical comparisons were performed using a Box-Cox transformation to normalize data variance, followed by one-factor analysis of variance (ANOVA) with Tukey's honestly significant difference post-hoc test.

Results

The Low group (1.5 mm diameter disk) containing the smallest EpiFix® sample was not significantly different from the no serum negative control (see bar graph in FIG. 2). Both the Medium group (4 mm diameter disk) and the High group (12×13 mm square, trimmed into 3-4 mm square pieces) were statistically higher than the no serum control (about 60% and 75% migration relative to control; see FIG. 2), indicating that EpiFix® stimulated cell migration. The High group was not significantly different from the Medium group. The results indicate that the EpiFix® product contains one or more factors that attract human mesenchymal stem cells.

Example 4

Stem Cell Recruitment in Mice Receiving EpiFix® Implants

A study was undertaken to determine whether EpiFix® implanted in normal mice causes recruitment of stem/progenitor cells, focusing on mouse hematopoietic stem cells (HSCs) and mouse mesenchymal stem cells (mouse MSCs).

Materials and Methods

EpiFix® products from six donors were used for implantation in normal mice. A 5×5 mm square of EpiFix® was surgically placed subcutaneously in 4 month old FVB/NJ mice (weighing between about 23.50 g and about 30 g). Four mice were implanted per sample per time point. The time points were 3, 7, 14 and 28 days. The negative controls were normal skin and sham operated mice (surgical incision but no implant). Decellularized dermal matrix (acellular dermal matrix; ADM) was used as the comparative implant (Type I collagen, no cytokines). The implant and overlying skin was harvested for fluorescence-activated cell sorting (FACS).

Implants and overlying skin were harvested, cut into 1 mm$^2$ sections, and incubated in a 0.15% dispase/0.075% collagenase solution at 37° C. for 1 hour. After centrifugation, samples were stained with a lineage antibody cocktail as described below. CD31 antibody was added followed by Alexa Fluor 647 anti-rat secondary antibody. Phycoerythrin-Cy7-conjugated anti-CD45 antibody was incubated last. Samples were prepared and analyzed as described below.

Samples were incubated with a lineage negative (lin$^-$) antibody cocktail (Ter119/CD4/CD8a/Gr-1/CD45R/CD11b) followed by phycoerythrin-Cy5 anti-rat secondary antibody. For mesenchymal stem cell analysis, conjugated antibodies were added against CD45 (phycoerythrin-Cy7) and Sca-1 (fluorescein isothiocyanate). For hematopoietic stem cell analysis, conjugated antibodies were added against CD45 (phycoerythrin-Cy7), c-Kit (phycoerythrin), and Sca-1 (fluorescein isothiocyanate). Samples were incubated with antibodies for 30 minutes and then washed by adding 5 volumes of 2% fetal bovine serum in phosphate-buffered saline with 2 mM ethylenediaminetetraacetic acid. Cells were centrifuged and then re-suspended in propidium iodide for 1 minute at 4° C. Samples were analyzed using an LSR Flow Cytometer. Using CellQuest software), samples were gated for lin$^-$/Sca-1$^+$/CD45$^-$ to define mesenchymal stem cells and for lin$^-$/Sca-1$^+$/c-Kit$^+$/CD45$^+$ to define hematopoietic stem cells.

Results

Figure 3A:
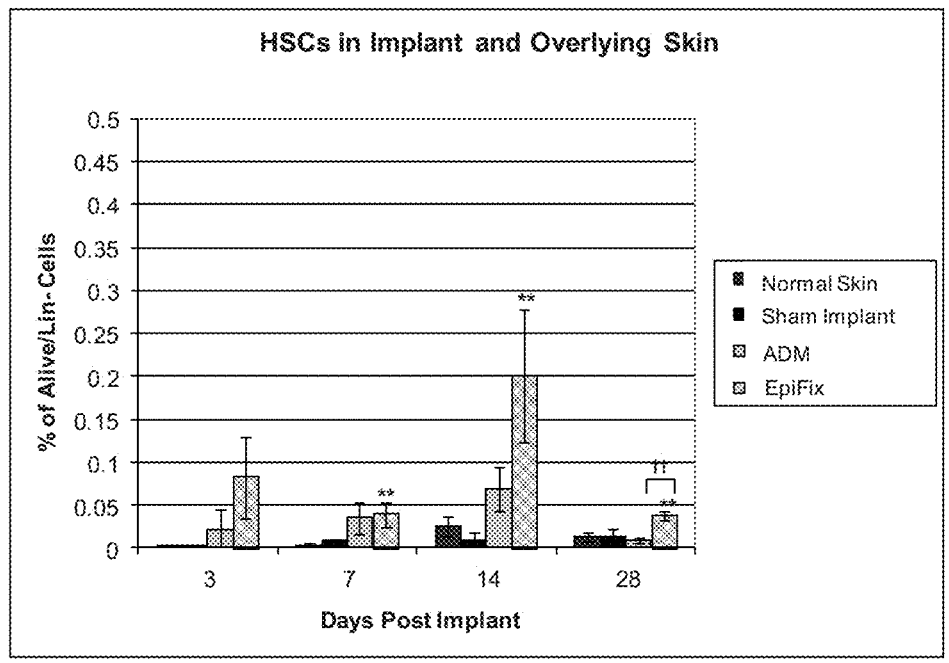
FIG. 3A shows a bar graph of percentage living/Lin⁻ mouse hematopoietic stem cells in normal skin, sham implant, acellular dermal matrix, and EpiFix® at 3, 7, 14, and 28 days post implant. Values shown are means +/- standard deviation, n=4 specimens.  indicates $p<0.05$ when comparing EpiFix® or control ADM to normal skin and sham implant via one-way ANOVA. †† indicates $p<0.05$ when comparing EpiFix® to control ADM via two tailed t-test.

Mouse HSCs were significantly increased following EpiFix® implantation compared to negative controls at days 7, 14 and 28 (see FIG. 3A). Mouse HSCs remained significantly increased in the EpiFix® samples at day 28 compared to ADM.

Figure 3B:
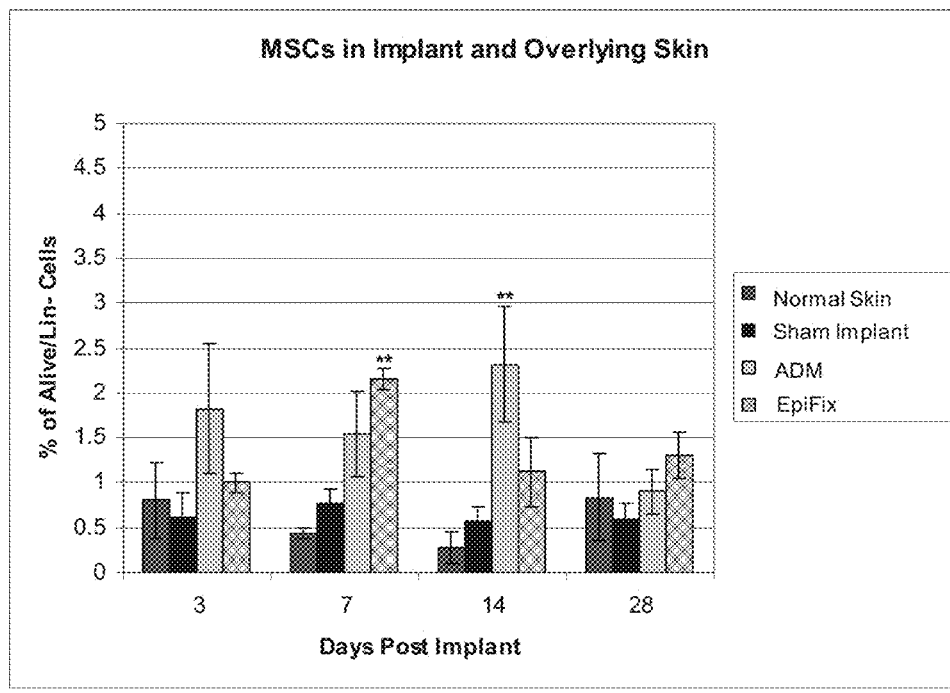
FIG. 3B shows a bar graph of percentage living/Lin⁻ mouse mesenchymal cells in normal skin, sham implant, acellular dermal matrix, and EpiFix® at 3, 7, 14, and 28 days post implant. Values shown are means+/- standard deviations, n=4 specimens.  indicates $p<0.05$ when comparing EpiFix® or control ADM to normal skin and sham implant via one-way ANOVA. Details are described in Example 4.

Mouse MSCs were significantly increased following EpiFix® implantation compared to negative controls at day 7 (see FIG. 3B). The average percentages of mouse MSCs were increased at all time points compared to negative controls.

Thus the data described above show that EpiFix® implants effectively recruit both HSCs and MSCs in vivo in normal mice. The data also show that EpiFix® leads to longer term HSC recruitment than acellular dermal matrix (ADM), supporting the hypothesis of a cytokine mediated effect of EpiFix®.

Example 5

Stem Cell Characterization in Mice Receiving EpiFix® Implants

A study was undertaken to characterize stem cells recruited to EpiFix® implantation sites in mice, using flow cytometry and immunohistochemistry.

Materials and Methods

Sterile, Purion® processed EpiFix® in a 5×5 mm square patch was implanted subcutaneously through a skin incision on the backs of sixteen 4 month old FVB/NJ mice. Identical skin incisions were made in another sixteen mice to function as a control treatment (sham). For comparison with a collagen scaffold, a 5×5 mm square patch of decellularized human dermis (acellular dermal matrix; ADM) was implanted subcutaneously on the backs of sixteen mice. Un-operated mice were used as a source of "normal" back skin for the analyses.

The surgical site was removed at 3, 7, 14 and 28 days following implantation for analyses of stem cells. Four animals/group were used at each time point. Stem cells were identified with two distinct methods: Fluorescence-activated cell sorting (FACS) and immunohistochemistry (IHC). For the FACS analysis, all cells were isolated from the amnion and associated regenerated tissue. The cells were fluorescently labeled with antibodies to specific stem cell markers. The identity and number of each cell type were determined with a flow cytometer.

For the immunohistochemical analyses, the membrane and associated regenerated tissue was fixed, sectioned for slides, and stained with specific antibodies to stem cells. Two antibodies were used for the immunohistochemistry: anti-CD34, which specifically detects hematopoietic progenitor cells (HPC), and reacts with dermal progenitor cells, endothelial cells, dendritic cells; and anti-CD31, which detects endothelial cells. The stained tissue sections were examined microscopically and the presence and number of specific stem cell types were measured. For the experimental analysis, the relative number of each cell type was counted. The results were calculated as the percentage of each cell type (no. of immunostained cells/total number of cells). Two areas were analyzed immunohistochemically for cell recruitment: the tissue surrounding the implant and the implant itself.

Results

Figure 4A:
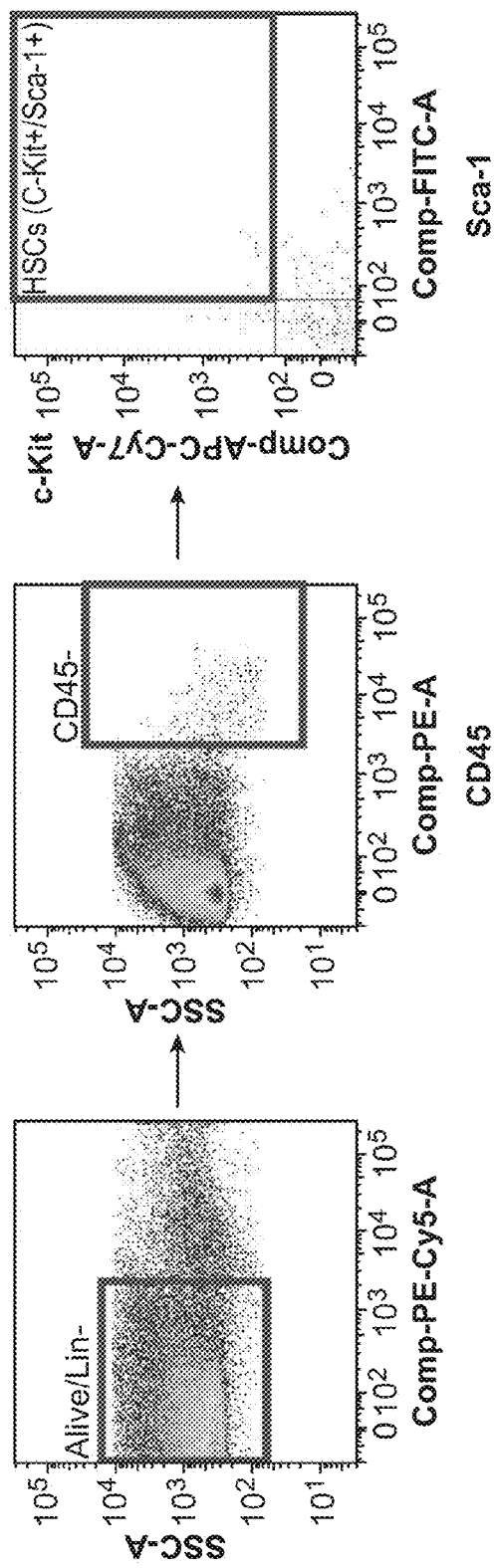
FIG. 4A shows representative FACS dot plots of cells detected using flow cytometry and fluorescent detection of CD45 and Sca-1.

Representative data from the FACS analyses are shown in FIG. 4A. The left panel shows the total number of cells in the sample. The middle panel shows the number of CD45 positive cells (in red box). The right panel shows the number of Sca-1 positive cells (in red box). CD45 and Sca-1 are specific markers for hematopoietic stem cells.

Figure 4B:
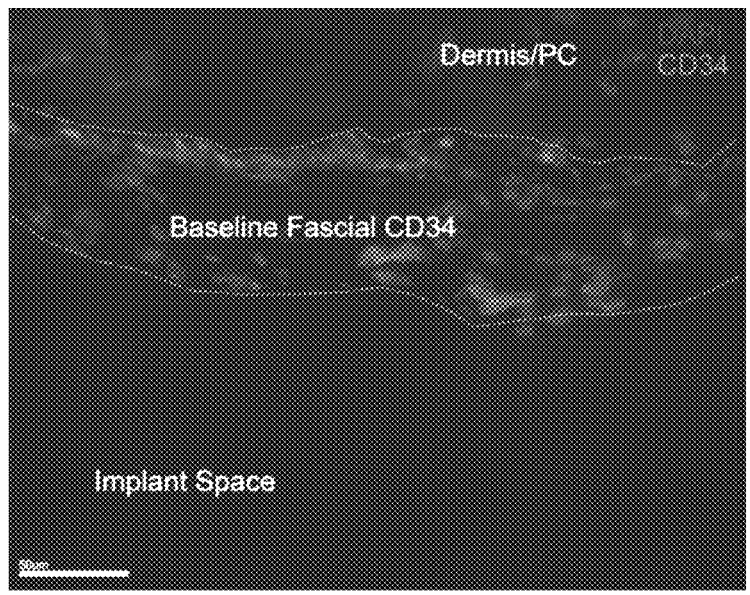
FIG. 4B shows photomicrograph of dermal tissue stained with DAPI which stains cell bodies, and CD34, which is a marker for hematopoietic stem cells. Details are described in Example 5.
Figure 5:
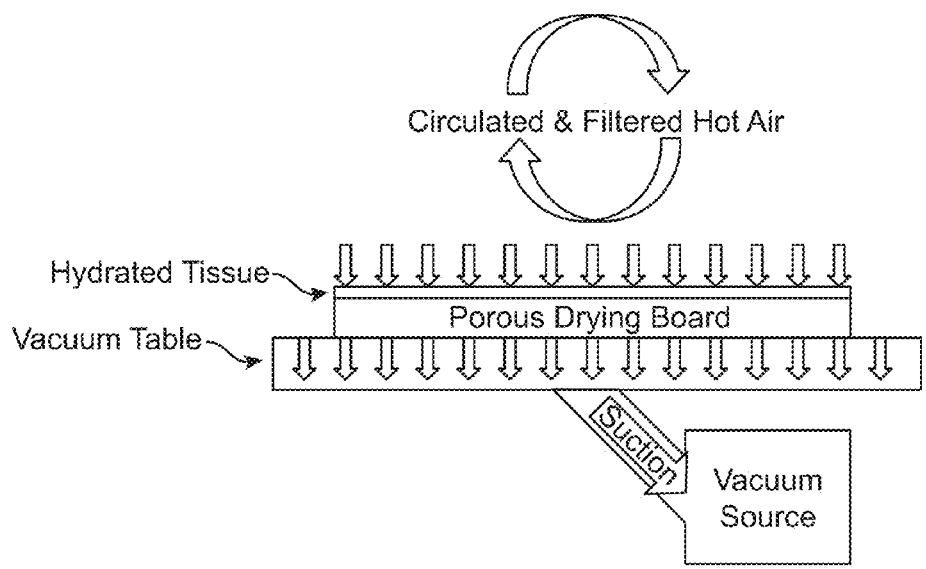
FIG. 5 shows a conceptual diagram of the dehydration device where the vacuum source provides suction that holds down the placental tissue and the drying board during circulated and filtered hot air cycle.
Figure 6:
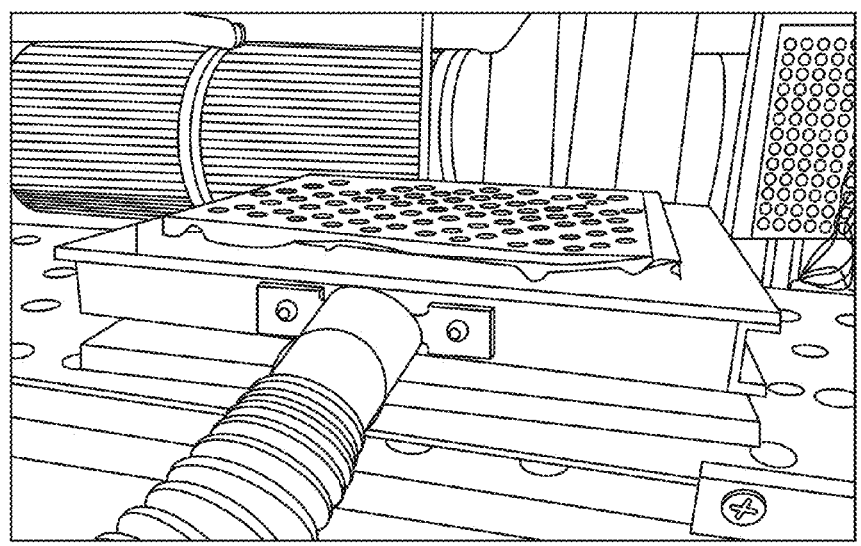
FIG. 6 shows a vacuum table attached to a dehydration chamber.
Figure 7:
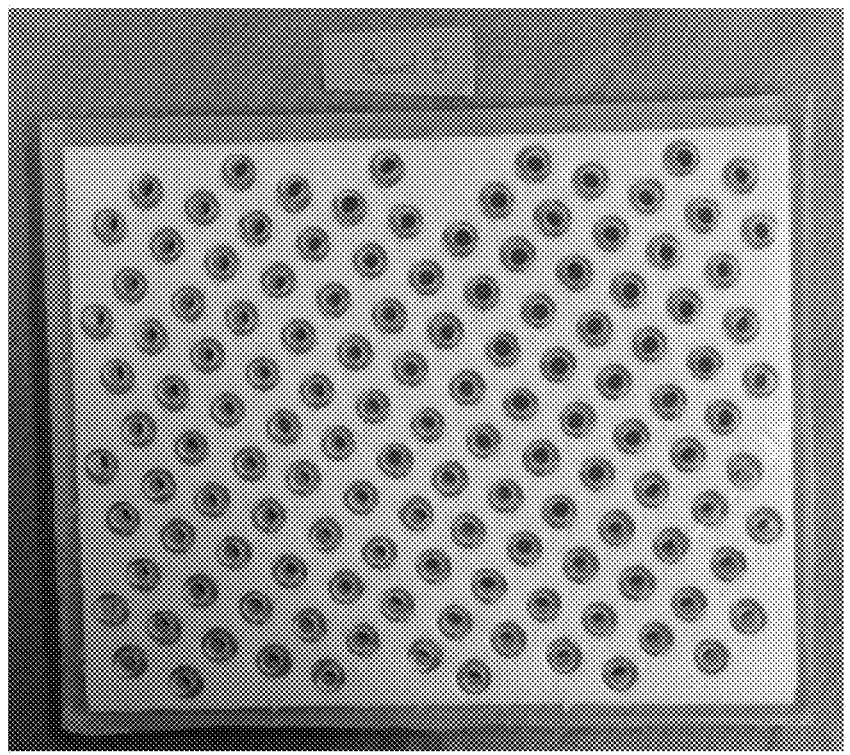
FIG. 7 shows a polycarbonate-silicone composite board which is composed of ¼ inch thick polycarbonate insert entirely surrounded by silicone.

FIG. 4B shows an exemplary immunohistochemistry image. The gray bar in the lower left corner represents 50 μm. The section was stained with DAPI (blue—stains all cells) and anti-CD34 (red). The place where the tissue is implanted in the experimental mice is shown for reference.

Hematopoietic progenitor cell (HPC) levels were significantly elevated in tissue surrounding EpiFix® implants at days 14 and 28 compared to negative controls. Hematopoietic progenitor cells were significantly increased in the tissue surrounding the EpiFix® implant at days 14 and 28 compared to collagen scaffold ADM control.

Progenitor cells were recruited into the EpiFix® implant. Intra-implant hematopoietic progenitor cells peaked at day 14 in the EpiFix® implant, and remained elevated at day 28. Average intra-implant hematopoietic progenitor cells were increased in the EpiFix® implant at days 14 and 28 compared to control ADM. Progenitor cells were not recruited into the ADM control implant.

Vascularization of the EpiFix® implant steadily increased from day 14 to day 28. The amount of new vessel formation in the EpiFix® implant was significantly greater than that in the ADM control on day 28.

These data establish that EpiFix® contains one or more factors that recruit both hematopoietic stem cells and mesenchymal stem cells to the site of injury. More of these stem cells were found in the EpiFix® membrane and associated regenerated tissue that in the sham or, more importantly, the control collagen scaffold. EpiFix® was significantly more effective than the control decellularized collagen scaffold in recruiting progenitor cells to colonize the implant site. There were more progenitor cells in the EpiFix® membrane than in the control collagen scaffold.

EpiFix® also induced new blood vessel formation in the associated regenerated tissue and the EpiFix® membrane itself. Vascularization in the EpiFix® membrane was significantly higher than in the collagen scaffold control.

Example 6

Test of Variable Vacuum Pressures and Drying Board Hole Sizes

This study demonstrates the operation of the vacuum pressure and drying board hole sizes to achieve the desirable tissue aesthetics.

Varying vacuum pressures and board hole sizes were tested in order to determine the minimum amount of pressure per board area required to hold down the amniotic tissue during dehydration. Using minimal pressure would increase system efficiency and reduce "bubble" size on the dried placental tissue grafts. Over a series of four experiments, vacuum pressure applied to drying tissue was incrementally decreased from 16 to 5 inches of water until tissue would no longer hold and stay flat, and instead shrink and wrinkle due to dehydration. For each experiment, the same composite board was used and temperature was kept constant at 45° C. Hole size was changed midway through the series of tests, from 6 mm to 4 mm in diameter. The table below details the recorded measurements and calculation of resulting pressure per board area. Binary "yes/no" outputs were also inserted to define the tissue holding threshold.

| Vacuum Holding Strength Calculations | | | | | | |
|---|---|---|---|---|---|---|
| No. of Holes | Hole Area (mm$^2$) | Vacuum (MPa) | Holding Strength (N) | Board Dimensions (mm) | Holding Pressure (Pa) | Tissue Held? |
| 1 | 132 | 28.27 | 0.004 | 14.93 | 220 | 160 | 424 | Yes |
| 2 | 132 | 12.56 | 0.004 | 6.64 | 220 | 160 | 188 | Yes |

-continued

Vacuum Holding Strength Calculations

| | No. of Holes | Hole Area (mm²) | Vacuum (MPa) | Holding Strength (N) | Board Dimensions (mm) | | Holding Pressure (Pa) | Tissue Held? |
|---|---|---|---|---|---|---|---|---|
| 3 | 132 | 12.56 | 0.0035 | 5.81 | 220 | 160 | 16.5 | Yes |
| 4 | 132 | 12.56 | 0.00125 | 2.07 | 220 | 160 | 5.89 | No |

Data obtained from the vacuum holding strength experiment shows that any pressure/are below 5.89 Pa was insufficient to stabilize the placental tissue on the drying board during the dehydration process. The threshold value of each parameter may be established by this experiment.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A method of eliciting stem cell recruitment and/or localization to a diseased or injured body part, the method comprising contacting a source of stem cells with a sufficient amount of modified placental tissue under conditions such that the placental tissue elutes an effective amount of stem cell recruiting factors so as to promote sufficient stem cell recruitment and/or localization proximate to said placental tissue to treat the diseased or injured body part.

2. The method of claim 1, wherein the source is ex vivo.

3. The method of claim 1, wherein the stem cells recruited by the composition are pluripotent stem cells.

4. The method of claim 1, wherein the placental tissue has a mass sufficient to recruit stem cells.

5. The method of claim 1, wherein the placental tissue comprises amnion.

6. The method of claim 5, wherein the amnion is selected from the group consisting of decellularized amnion, deepithelialized amnion retaining a fibroblast layer and amnion containing both epithelial cells and a fibroblast layer.

7. The method of claim 1, wherein the stem cell recruitment and/or localization occurs within about one day to at least 7 days after contacting with the placental tissue.

* * * * *